US008279999B2

United States Patent
Kondo et al.

(10) Patent No.: US 8,279,999 B2
(45) Date of Patent: Oct. 2, 2012

(54) X-RAY CT APPARATUS AND A METHOD OF CONTROLLING THE X-RAY CT APPARATUS

(75) Inventors: Gen Kondo, Otawara (JP); Hisashi Yasuda, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 214 days.

(21) Appl. No.: 12/707,089

(22) Filed: Feb. 17, 2010

(65) Prior Publication Data

US 2010/0215141 A1     Aug. 26, 2010

(30) Foreign Application Priority Data

Feb. 26, 2009  (JP) ................................. 2009-043611
Dec. 25, 2009  (JP) ................................. 2009-293700

(51) Int. Cl.
*G01N 23/00*     (2006.01)
(52) U.S. Cl. ............................................. 378/16; 378/4
(58) Field of Classification Search ................. 378/4–20
See application file for complete search history.

(56) References Cited

U.S. PATENT DOCUMENTS

| 5,832,051 A | * | 11/1998 | Lutz | 378/8 |
| 2008/0317196 A1 | * | 12/2008 | Imai et al. | 378/8 |
| 2009/0028289 A1 |   | 1/2009 | Tsuyuki et al. | |
| 2009/0097611 A1 | * | 4/2009 | Nishide et al. | 378/5 |

FOREIGN PATENT DOCUMENTS

JP     2009-28065     2/2009

* cited by examiner

*Primary Examiner* — Hoon Song
(74) *Attorney, Agent, or Firm* — Oblon, Spivak, McClelland, Maier & Neustadt, L.L.P.

(57) ABSTRACT

An X-ray CT apparatus includes an X-ray generator and an X-ray detector. The X-ray generator and the X-ray detector rotate about a subject. A controller controls the timing of exposing X-rays from the X-ray generator. The controller controls the collection timing for the projection data used by the X-ray detector and causes the X-ray detector to continuously collect the projection data at the specified collection timing. The controller causes additional information representing the state of exposure of the X-rays to be added to each projection data that has been collected by the X-ray detector at said specified collection timing.

12 Claims, 4 Drawing Sheets

X-RAY CT APPARATUS AND A METHOD OF CONTROLLING THE X-RAY CT APPARATUS

BACKGROUND OF THE INVENTION

1. Field of the Invention

The present invention relates to an X-ray computed tomography (CT) apparatus that collects projection data by exposing X-rays to a subject and generates an image based on the projection data, and relates to a method of controlling the X-ray CT apparatus

2. Description of the Related Art

The X-ray CT apparatus includes an X-ray tube and an X-ray detector, which are arranged opposite to one another by sandwiching a subject. The X-ray CT apparatus rotates the X-ray tube and the X-ray detector about the subject while exposing X-rays from the X-ray tube and detecting, in the X-ray detector, X-rays transmitted through the subject. The data detected by the X-ray detector is collected as projection data in a data acquisition system (DAS), and the collected projection data is used to generate an image of the subject. For example, the projection data is collected by rotating the X-ray tube and the X-ray detector by 360° or (180°+fan angle) and the image is generated based on the projection data over 360° or (180°+fan angle).

A set of detection data detected at an angle relative to the subject by the X-ray detector having a plurality of detection elements is referred to as a "view". A single rotation of the X-ray tube and the X-ray detector about the subject to collect the projection data of a plurality of views necessary to reconstruct an image is referred to as a "scan". For example, when the projection data for 1 view is collected for each 1°, the projection data for 360 views is obtained for 1 scan and the image is reconstructed using the projection data of these 360 views.

The collection of the projection data is continuously performed by the data acquisition system (DAS) while X-rays may be intermittently exposed from the X-ray tube. When the image is reconstructed using the projection data collected by such imaging, it is necessary to reconstruct the image using the projection data collected over a period during which X-rays have actually been exposed. For example, in cardiac testing, imaging may be performed by switching the X-ray exposure on and off according to the subject's heartbeat (prospective gating scan) (e.g., Japanese Unexamined Patent Application Publication No. 2009-28065). In this case, it is necessary to reconstruct the image using the projection data collected by the data acquisition system (DAS) over a period during which X-rays have actually been exposed.

In the prior art, an X-ray detector (Ref detector) that is to be a reference is provided to the X-ray CT apparatus and a detection value (count value) detected by the Ref detector is added to the projection data for each view. Then, based on the count value detected by the Ref detector and added to each projection data for 1 view, it is determined whether X-rays have been exposed and it is thereby determined whether the projection data has been collected during a period in which X-rays have been exposed. In addition, when the exposure amount of the subject during the actual imaging is obtained, the dose is calculated by counting the views for which X-rays have been exposed.

In addition, in a scan mode in which X-rays are exposed while modulating the X-ray output (mA), the level of X-ray output (mA) can be judged by a detection value detected by the Ref detector but the actual X-ray output value (mA value) cannot be judged. Therefore, the dose is calculated using the X-ray output value that has been set by the X-ray CT apparatus during imaging planning.

In the prior art, by setting a threshold relative to the detection value (count value) of the Ref detector, it is determined whether the projection data for each view has been collected during a period in which X-rays have been exposed. However, the count value of the Ref detector is varied according to each Ref detector. In addition, the count value of the Ref detector is varied according to the conditions for X-ray exposures. Therefore, it is difficult to set a threshold suitable for determining whether X-rays have been exposed or not. For example, it is necessary to take into consideration the individual differences of the Ref detectors and the variations in the individual differences of the X-ray tube. In addition, the count value of the Ref detector is varied according to the tube voltage. Therefore, it is difficult to set a suitable threshold. In addition, by taking into consideration the offset value of the Ref detector and the data acquisition system (DAS), it is necessary to decide the threshold for determining the ON and OFF states of the X-ray exposure. Moreover, it is possible to make an error in determining the ON and OFF states of the X-ray exposure if the X-ray tube is unstable and may, for example, instantaneously generate a discharge or undergo current fluctuations.

If there is an error in determining the ON and OFF states of the X-ray exposure, the number of views necessary for reconstruction may not be obtained or the image may be reconstructed using the projection data of views that have been collected when the X-rays were in the OFF state.

Furthermore, using the detection value (count value) of the Ref detector makes it possible to determine only the ON and OFF states of the X-ray exposure. In a scan mode in which the X-ray output (mA) is modulated, the actual X-ray output value cannot be judged. Therefore, it is difficult to accurately calculate the actual exposure dose.

SUMMARY OF THE INVENTION

The present invention is intended to provide an X-ray CT apparatus and a method of controlling the X-ray CT apparatus that allows more precise determination of whether projection data is collected under an X-ray exposure state.

A first aspect of the present invention is an X-ray CT apparatus comprising: an X-ray generator; an X-ray detector, arranged opposite to said X-ray generator by sandwiching a subject, configured to collect, as projection data, X-rays that have been exposed from said X-ray generator and transmitted through said subject at a specified collection timing, wherein said X-ray generator and said X-ray detector are configured to be rotatable about said subject; and a controller configured to control the timing of exposing said X-rays from said X-ray generator so as to supply a voltage and current to said X-ray generator to cause said X-ray generator to expose said X-rays when said X-ray generator exposes said X-rays, to control the collection timing for said projection data used by said X-ray detector to cause said X-ray detector to continuously collect said projection data at said specified collection timing, and to cause additional information representing the state of exposure of said X-rays to be added to each projection data that has been collected by said X-ray detector at said specified collection timing.

According to the first aspect of the invention, additional information indicating the state of the X-ray exposure is added to each set of projection data, so as to allow more precise determination of whether projection data is collected under an X-ray exposure state.

A second aspect of the present invention is an method of controlling an X-ray CT apparatus, the X-ray CT apparatus comprising: an X-ray generator; an X-ray detector, arranged opposite to said X-ray generator by sandwiching a subject, configured to collect, as projection data, X-rays that have been exposed from said X-ray generator and transmitted through said subject at a specified collection timing, wherein said X-ray generator and said X-ray detector are configured to be rotatable about said subject and the method comprising: controlling the timing of exposing said X-rays from said X-ray generator so as to supply a voltage and current to said X-ray generator to cause said X-ray generator to expose said X-rays when said X-ray generator exposes said X-rays; controlling the collection timing for said projection data used by said X-ray detector to cause said X-ray detector to continuously collect said projection data at said specified collection timing; and causing additional information representing the state of exposure of said X-rays to be added to each projection data that has been collected by said X-ray detector at said specified collection timing.

DETAILED DESCRIPTION OF THE EMBODIMENTS

Figure 1:
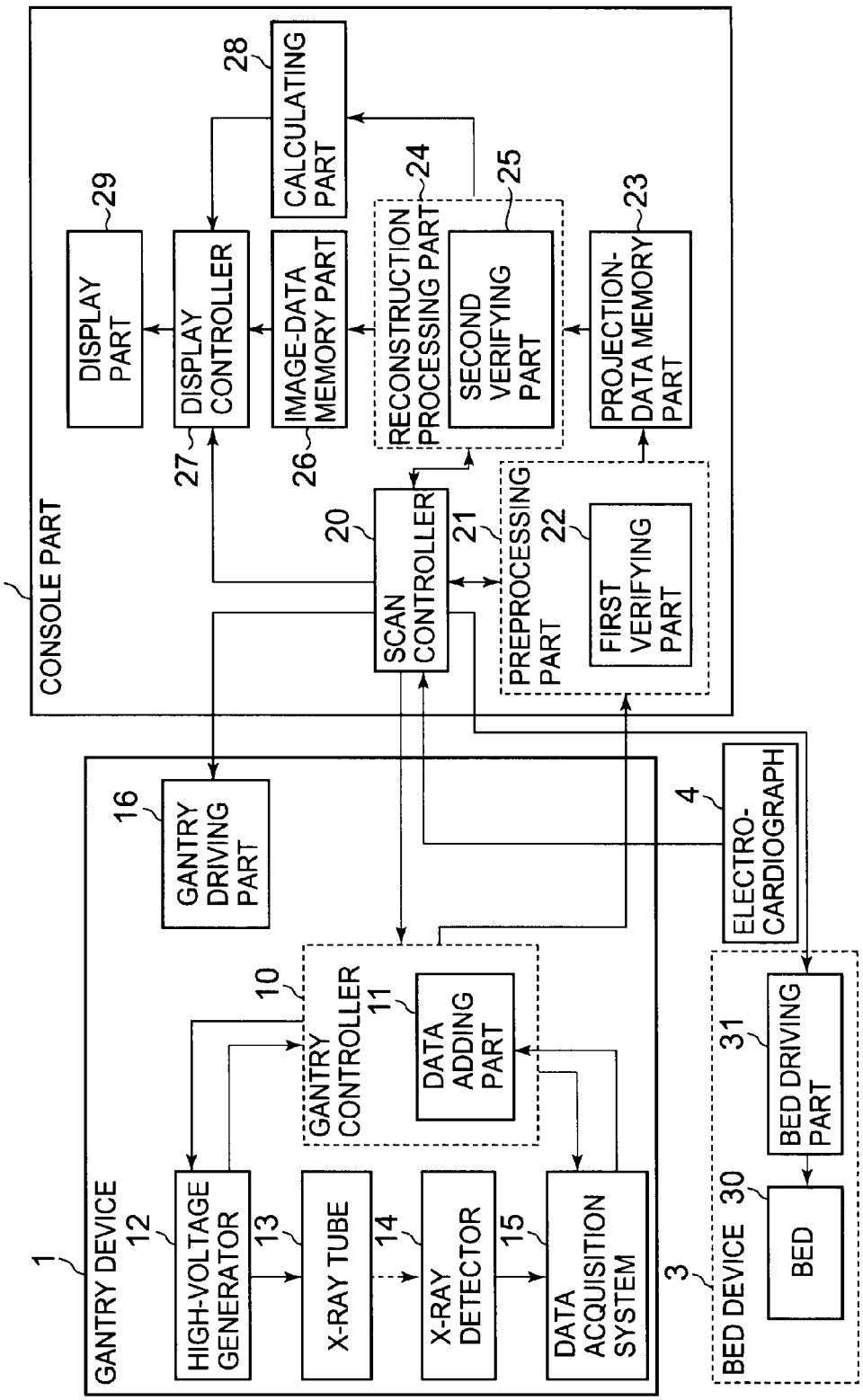
FIG. 1 is a block diagram of an X-ray CT apparatus according to the embodiment of the present invention.

An X-ray CT apparatus and a method of controlling the X-ray CT apparatus according to an embodiment of the present invention will be described with reference to FIG. 1.

The X-ray CT apparatus according to an embodiment of the present invention comprises a gantry device 1, a console part 2, and a bed device 3. The gantry device 1 comprises an X-ray tube 13 and a rotation gantry (not shown) that houses an X-ray detector 14, and collects projection data. The projection data is output to the console part 2 and is subjected to a reconstruction process. The bed device 3 comprises a bed 30 on which the subject is placed.

The gantry device 1 is provided with the X-ray tube 13 and the X-ray detector 14 that is arranged opposite to the X-ray tube 13. The X-ray detector 14 includes a plurality of detection elements arranged in two mutually orthogonal directions (a slice direction (body-axis direction) and a channel direction (circumferential direction)) to make a two-dimensional X-ray detector. An X-ray detector in which a plurality of detection elements is arranged in the channel direction (circumferential direction) may be used for the X-ray detector 14.

A high-voltage generator 12 supplies, to the X-ray tube 13, a tube voltage and tube current for exposing X-rays under the control of a gantry controller 10. X-rays are thus generated from the X-ray tube 13. It is noted that one example of an "X-ray generator" of the present invention comprises the X-ray tube 13 and the high-voltage generator 12.

A data acquisition system (DAS) 15 is connected to the X-ray detector 14. The data acquisition system 15 includes a data collection element arranged in the same manner as each detection element of the X-ray detector 14. The data acquisition system 15 collects an X-ray signal detected by the X-ray detector 14 by matching it with a data-collection controlling signal (view trigger signal (VT signal)) output by the gantry controller 10. The data collected by the data acquisition system 15 is the projection data. It is noted that one example of an "X-ray detector" comprises the X-ray detector 14 and the data acquisition system 15.

X-ray beams exposed from the X-ray tube 13 are irradiated to the subject placed on the bed 30 through an X-ray collimator (not shown) provided with a slit having a specified width. The X-ray beams transmitted through the subject are detected by the X-ray detector 14.

The signal detected by the X-ray detector 14 is collected as the projection data by the data acquisition system 15.

A gantry driving part 16 causes the rotation gantry (not shown) to be rotated based on gantry control signals output by a scan controller 20. The rotation gantry is thus rotated about the center of rotation.

The scan controller 20 in the console part 2 outputs control data to the gantry controller 10 in the gantry device 1. The control data includes information representing the conditions for X-ray exposure and information representing the exposure timing. The exposure conditions include a tube current value and a tube voltage value, which are supplied to the X-ray tube 13. The irradiation timing represents a timing for switching the X-ray exposure from the X-ray tube 13 on and off. The information representing the irradiation timing includes an ON signal representing X-ray exposure and an OFF signal representing discontinuation of X-ray exposure. In addition, the scan controller 20 outputs the gantry controlling signal to the gantry driving part 16 in order to stably rotate the rotation gantry at a constant speed.

The gantry controller 10 outputs, to a high-voltage generator 12, the control data including the information representing the conditions for X-ray exposure and information representing the exposure timing.

In addition, the gantry controller 10 generates a data-collection controlling signal (View Trigger signal (VT signal)) representing the collection timing of the projection data used by the data acquisition system 15 and outputs the data-collection controlling signal to the data acquisition system 15 and the high-voltage generator 12. Moreover, the gantry controller 10 generates a data-collection starting signal (BGN) representing the start of the collection of the projection data and outputs the data-collection starting signal to the data acquisition system 15.

The high-voltage generator 12 receives the VT signal and the control data (exposure condition and irradiation timing) from the gantry controller 10. In accordance with the information representing the irradiation timing (ON/OFF signal of the X-ray exposure), the high-voltage generator 12 supplies the tube current and tube voltage represented by the exposure conditions. In other words, the high-voltage generator 12 supplies the tube current and tube voltage to the X-ray tube 13 during periods in which the irradiation timing indicates that the X-ray exposure is in the ON state and causes the X-ray tube 13 to expose X-rays. On the other hand, the high-voltage generator 12 stops supplying the tube current and tube voltage to the X-ray tube 13 during periods in which the irradiation timing indicates that the X-ray exposure is in the OFF state and causes the X-ray tube 13 to stop the X-ray exposure. In addition, in accordance with the ON/OFF signals of the X-ray exposure, the high-voltage generator 12 generates X-ray output information (X-ray status information) representing the tube current value (mA) and tube voltage value (kV) that have actually been provided to the X-ray tube and outputs the X-ray status information to the gantry controller 10. In other words, in accordance with the ON/OFF signals of the X-ray exposure, the high-voltage generator 12 generates the X-ray status information representing the tube current value and tube voltage value used when the X-ray tube 13 has actually exposed X-rays and outputs the X-ray status information to the gantry controller 10. The high-voltage generator 12 samples the X-ray status information and outputs it to the gantry controller 10 in synchronization with the VT signal representing the collection timing of the projection data used by the data acquisition system 15.

The high-voltage generator 12 may include either the tube current value or the tube voltage value in the X-ray status information or may include both values in the X-ray status information. In other words, the high-voltage generator 12 may include only the tube current value in the X-ray status information, may include only the tube voltage value in the X-ray status information, or may include the tube current value and the tube voltage value in the X-ray status information.

The data acquisition system 15 collects, as the projection data, the X-rays (X-ray signal) detected by the X-ray detector 14 in synchronization with the VT signal output by the gantry controller 10.

The data acquisition system 15 outputs the projection data to the gantry controller 10. Upon receiving the data-collection starting signal (BGN) from the gantry controller 10, the data acquisition system 15 starts the collection of the projection data and collects the projection data in synchronization with the VT signal. It is noted that the collection timing of the projection data synchronized with the VT signal corresponds to one example of the "specified collection timing" of the present invention.

(Data Adding Part 11)

The gantry controller 10 comprises a data adding part 11. The data adding part 11 adds, as extra data (additional information), the X-ray status information output by the high-voltage generator 12 as well as the ON/OFF signals (X-ray controlling data) of the X-ray exposure to the projection data for each view output by the data acquisition system 15. The data adding part 11 adds, to the projection data for each view, the X-ray status information generated by a VT signal identical to the VT signal representing the collection timing of the projection data for each view as well as the X-ray controlling data.

For example, the data adding part 11 adds the ON signal of the X-ray exposure (X-ray controlling data) as well as the X-ray status information to the projection data collected at a timing at which the X-ray exposure has been collected in the ON state. In addition, the data adding part 11 adds the OFF signal of the X-ray exposure (X-ray controlling data) to the projection data collected at a timing at which the X-ray exposure has been collected in the OFF state. The gantry controller 10 outputs, to a preprocessing part 21, each projection data to which the extra data has been added. It is noted that the scan controller 20 and the gantry controller 10 correspond to one example of a "controller" of the present invention. In addition, the ON/OFF signals (X-ray controlling data) of the X-ray exposure correspond to one example of "exposure information representing whether X-rays have been exposed" of the present invention.

(Preprocessing Part 21)

The preprocessing part 21 comprises a first verifying part 22.

The first verifying part 22 receives, from the gantry controller 10, each projection data to which the extra data has been added. The first verifying part 22 verifies the X-ray status information (X-ray output information) and the X-ray controlling data (ON/OFF signals of the X-ray exposure) that are included in the extra data. First, the first verifying part 22 determines whether each projection data has been collected during X-ray exposure based on the ON/OFF signals of the X-ray exposure represented by the X-ray controlling data. Specifically, when the ON signal of the X-ray exposure is added to the projection data as the X-ray controlling data, the first verifying part 22 determines that the projection data has been collected during X-ray exposure. In addition, when the OFF signal of the X-ray exposure is added to the projection data as the X-ray controlling data, the first verifying part 22 determines that the projection data has been collected during discontinuation of X-ray exposure.

Moreover, for projection data to which the ON signal of the X-ray exposure is added (projection data that has been collected during X-ray exposure), the first verifying part 22 determines whether the tube current value and tube voltage value represented by the X-ray status information are within the specified range that has been preliminarily set. This specified range is a criterion for determining whether the tube current value and tube voltage value are normal values during X-ray exposure. An operator may be allowed to arbitrarily change this specified range using an operating part (not shown). The first verifying part 22 determines that the X-ray exposure has been performed with a normal tube current value and tube voltage value when the tube current value and tube voltage value are within the specified range. In other words, the first verifying part 22 determines that projection data in which the tube current value and tube voltage value are within the specified range is projection data that has been collected during normal X-ray exposure. In addition, the first verifying part 22 determines that projection data in which the tube current value and tube voltage value are not within the specified range is projection data that has not been collected during normal X-ray exposure.

Then, the preprocessing part 21 performs preprocessing, such as sensitivity correction and X-ray intensity correction, for the projection data in which the tube current value and tube voltage value are within the specified range. In other words, the preprocessing part 21 performs preprocessing for projection data that has been collected during X-ray exposure with a normal tube current value and tube voltage. The preprocessing part 21 causes a projection-data memory part 23 to store the projection data for which the preprocessing has been performed.

In addition, the preprocessing part 21 may delete projection data for which the preprocessing has not been performed. In other words, the preprocessing part 21 may delete projection data to which the OFF signal of the X-ray exposure is added as the X-ray controlling data (projection data that has been collected with X-ray exposure in the OFF state). Moreover, even for projection data to which the ON signal of the X-ray exposure is added as the X-ray controlling data (projection data that has been collected with X-ray exposure in the ON state), the preprocessing part 21 may delete the projection data in which the tube current value and tube voltage value are not within the specified range (projection data that has not been collected during X ray exposure with a normal tube current value and tube voltage value).

In other words, the preprocessing part 21 performs preprocessing for only projection data that has been collected with X-ray exposure in the ON state (i.e., during X-ray exposure) and that has been collected during X-ray exposure with a normal tube current value and tube voltage value and causes the projection-data memory part 23 to store the projection data for which the preprocessing has been performed.

It is noted that the first verifying part 22 may, using only the tube current value, determine whether the projection data has been collected during normal X-ray exposure. In other words, the first verifying part 22 may determine that the projection data has been collected during normal X-ray exposure when the tube current value is within the specified range. In addition, the first verifying part 22 may, by using not the X-ray controlling data (ON/OFF signals of the X-ray exposure) but the tube current value, determine whether the projection data has been collected during normal X-ray exposure. In other words, the first verifying part 22 may determine that the projection data has been collected during normal X-ray exposure without making a determination using the X-ray controlling data when the tube current value is within the specified range.

(Error Sensing)

In addition, even for projection data to which the ON signal of the X-ray exposure is added (projection data that has been collected with X-ray exposure in the ON state), the preprocessing part 21 may output an error signal representing an error to the scan controller 20 if the projection data is data in which the tube current value represented by the X-ray status information is not within the specified range (i.e., the projection data has not been collected during X-ray exposure with a normal tube current value). For example, even if the X-ray exposure is in the ON state (i.e., during X-ray exposure), when problems such as tube current shortages due to a discharge, etc. occur, the tube current value represented by the X-ray status information maybe not within the specified range that has been preliminarily set. In this case, the preprocessing part 21 senses the problem in the tube current value and outputs an error signal to the scan controller 20. Upon receiving the error signal from the preprocessing part 21, the scan controller 20 issues an instruction to cancel the scan to the gantry controller 10.

Upon receiving the instruction to cancel the scan from the scan controller 20, in accordance with that instruction, the gantry controller issues an instruction to cancel the X-ray exposure to the high-voltage generator 12 and issues an instruction to cancel the data acquisition to the data acquisition system 15.

In this way, the scan (imaging) is cancelled. In addition, the operator may be informed of the problem in the X-ray status. For example, the scan controller 20 outputs the error signal to a display controller 27. Upon receiving the error signal from the scan controller, the display controller 27 causes a display part 29 to display a message and graphic showing the problem in the X-ray status. Moreover, the X-ray CT apparatus may be provided with a speaker to generate a sound indicating the problem in the X-ray status. It is noted that the display controller 27 and the speaker correspond to one example of an "informing part" of the present invention.

(Reconstruction Processing Part 24)

A reconstruction processing part 24 retrieves, from the projection-data memory part 23, the projection data for which the preprocessing has been performed and reconstructs the image data by performing a back-projection process for projection data for which the preprocessing has been performed. The reconstruction processing part 24 outputs the reconstructed image data to an image-data memory part 26. The image-data memory part 26 stores the reconstructed image data.

The projection-data memory part 23 stores the projection data that has been collected with X-ray exposure in the ON state (i.e., during X-ray exposure) and that has been collected during X-ray exposure with a normal tube current value and tube voltage value.

Accordingly, the reconstruction processing part 24 can reconstruct only the projection data that has been collected during X-ray exposure by retrieving the projection data stored in the projection-data memory part 23 and reconstructing the image data.

(Second Verifying Part 25)

In the example described above, the first verifying part 22 in the preprocessing part 21 verifies the X-ray status information and the X-ray controlling data (ON/OFF signals of the X-ray control) that are included in the extra data added to the projection data for each view.

Instead of the first verifying part 22 performing this verification, the second verifying part 25 in the reconstruction processing part 24 may perform this verification. In this case, the preprocessing part 21 performs preprocessing, such as sensitivity correction and X-ray intensity correction, for the projection data for all views without verifying the extra data. The projection data for which the preprocessing has been performed by the preprocessing part 21 is stored in the projection-data memory part 23.

The second verifying part 25 in the reconstruction processing part 24 retrieves, from the projection-data memory part 23, each projection data for which the preprocessing has been performed and verifies the X-ray status information and X-ray controlling data (ON/OFF signal of the X-ray exposure) that are included in the extra data added to each projection data. First, the second verifying part 25 determines whether each projection data has been collected during X-ray exposure based on the ON/OFF signal of the X-ray exposure represented by the X-ray controlling data. As with the first verifying part 22 described above, when the ON signal of the X-ray exposure is added to the projection data, the second verifying part 25 determines that the projection data has been collected during X-ray exposure. On the other hand, when the OFF signal of the X-ray exposure is added to the projection data, the second verifying part 25 determines that the projection data has been collected during discontinuation of X-ray exposure.

In addition, for projection data to which the ON signal of the X-ray exposure is added (projection data that has been collected during X-ray exposure), the second verifying part 25 determines whether the tube current value and tube voltage value represented by the X-ray status information are within the specified range that has been preliminarily set. As described above, this specified range is a criterion for determining whether the tube current value and tube voltage value are normal values during X-ray exposure. The second verifying part 25 determines that the X-ray exposure has been performed with a normal tube current value and tube voltage value when the tube current value and tube voltage value represented by the X-ray status information are within the specified range. In other words, the second verifying part 25 determines that projection data in which the tube current value and tube voltage value are within the specified range is projection data that has been collected during normal X-ray exposure. In addition, the second verifying part 25 determines that projection data in which the tube current value and tube voltage value are not within the specified range is projection data that has not been collected during normal X-ray exposure.

Then, the reconstruction processing part 24 reconstructs the image data by performing a back-projection process for projection data in which the tube current value and tube voltage value are within the specified range. In other words, the reconstruction processing part 24 reconstructs the image data by performing a back-projection process for projection data that has been collected during X-ray exposure with a normal tube current value and tube voltage value. The reconstruction processing part 24 outputs the reconstructed image data to an image-data memory part 26. The image-data memory part 26 stores the reconstructed image data.

The second verifying part 25 may determine whether the projection data has been collected during normal X-ray exposure using only the tube current in the same manner as the first verifying part 22.

In addition, the second verifying part 25 may determine whether the projection data has been collected during normal X-ray exposure by using not the X-ray controlling data but the tube current in the same manner as the first verifying part 22.

It is noted that the preprocessing part 21 and the reconstruction processing part 24 correspond to one example of an "image generator" of the present invention.

(Error Sensing)

In addition, even for projection data to which the ON signal of the X-ray exposure is added (projection data that has been collected with X-ray exposure in the ON state), the reconstruction processing part 24 may output an error signal representing an error to the scan controller 20 if the projection data is data in which the tube current value and tube voltage value represented by the X-ray status information are not within the specified range (i.e., the projection data has not been collected during X-ray exposure with a normal tube current value). Upon receiving the error signal from the reconstruction processing part 24, the scan controller 20 issues an instruction to cancel the scan to the gantry controller 10. Upon receiving the instruction to cancel the scan from the scan controller 20, the gantry controller 10, in accordance with that instruction, issues an instruction to cancel the X-ray exposure to the high-voltage generator 12 and issues an instruction to cancel the data acquisition to the data acquisition system 15. In this way, the scan is cancelled. In addition, the operator may be informed of the problem in the X-ray status. For example, the scan controller 20 outputs an error signal to the display controller 27. Upon receiving the error signal from the scan controller, the display controller 27 causes the display part 29 to display a message and graphic showing the problem in the X-ray status.

In this embodiment, either the first verifying part 22 or the second verifying part 25 may be provided in the X-ray CT apparatus. In other words, when the first verifying part 22 is provided in the preprocessing part 21, the second verifying part 25 may be excluded from the reconstruction processing part 24. In addition, when the second verifying part 25 is provided in the reconstruction processing part 24, the first verifying part 22 may be excluded from the preprocessing part 21. It is noted that the first verifying part 22 and the second verifying part 25 correspond to one example of an "identifying part" of the present invention.

(Display Controller 27)

The display controller 27 retrieves the image data from the image-data memory part 26 and causes the display part 29 to display the image based on the image data.

(Calculating Part 28)

A calculating part 28 calculates the dose using the tube current value (mA) for each view used for the reconstruction process. For example, the reconstruction processing part 24 outputs, to the calculating part 28, the tube current value (mA) represented by the X-ray status information that is added to each projection data used for reconstruction. The calculating part 28 receives the tube current value (mA) from the reconstruction processing part 24 and calculates the dose. Specifically, the calculating part 28 obtains the dose (mAs=mA× imaging period) based on the tube current value (mA) and the imaging period of the projection data for each view. The calculating part 28 outputs the dose information representing the dose (mAs) to the display controller 27. The display controller 27 causes the display part 29 to display the value of the dose (mAs) obtained by the calculating part 28. It is noted that the calculating part 28 corresponds to one example of a "calculating part" of the present invention.

(Bed Device 3)

The bed device 3 comprises a bed 30 and a bed driving part 31.

The bed 30 comprises a bed top board on which the subject is placed and a bed base that supports the bed top board. The bed top board may be moved by the bed driving part 31 in the body-axis direction (slice direction) of the subject. The bed base may cause the bed top board to be moved in the vertical direction by a bed driving part 31.

It is noted that the gantry controller 10, the scan controller 20, the preprocessing part 21, the reconstruction processing part 24, the display controller 27, and the calculating part 28 may comprise, as one example, a processing device (not shown), such as a CPU (Central Processing Unit), and a storage device (not shown), such as a ROM (Read Only Memory), RAM (Random Access Memory), or HDD (Hard Disk Drive). The storage device stores a gantry controlling program for executing the functions of the gantry controller 10, a scan controlling program for executing the functions of the scan controller 20, a preprocessing program for executing the functions of the preprocessing part 21, a reconstruction processing program for executing the functions of the reconstruction processing part 24, a display controlling program for executing the functions of the display controller 27, and a calculating program for executing the functions of the calculating part 28. In addition, the gantry controlling program includes a data adding program for executing the functions of the data adding part 11. Moreover, the preprocessing program includes a first verifying program for executing the functions of the first verifying part 22. Furthermore, the reconstruction processing program includes a second verifying program for executing the functions of the second verifying part 25. The processing apparatus, such as a CPU, executes each program and thereby executes the functions of each part.

Now, a series of operations performed by the X-ray CT apparatus according to this embodiment will be described with reference to the timing chart shown in FIG. 2.

Figure 2:
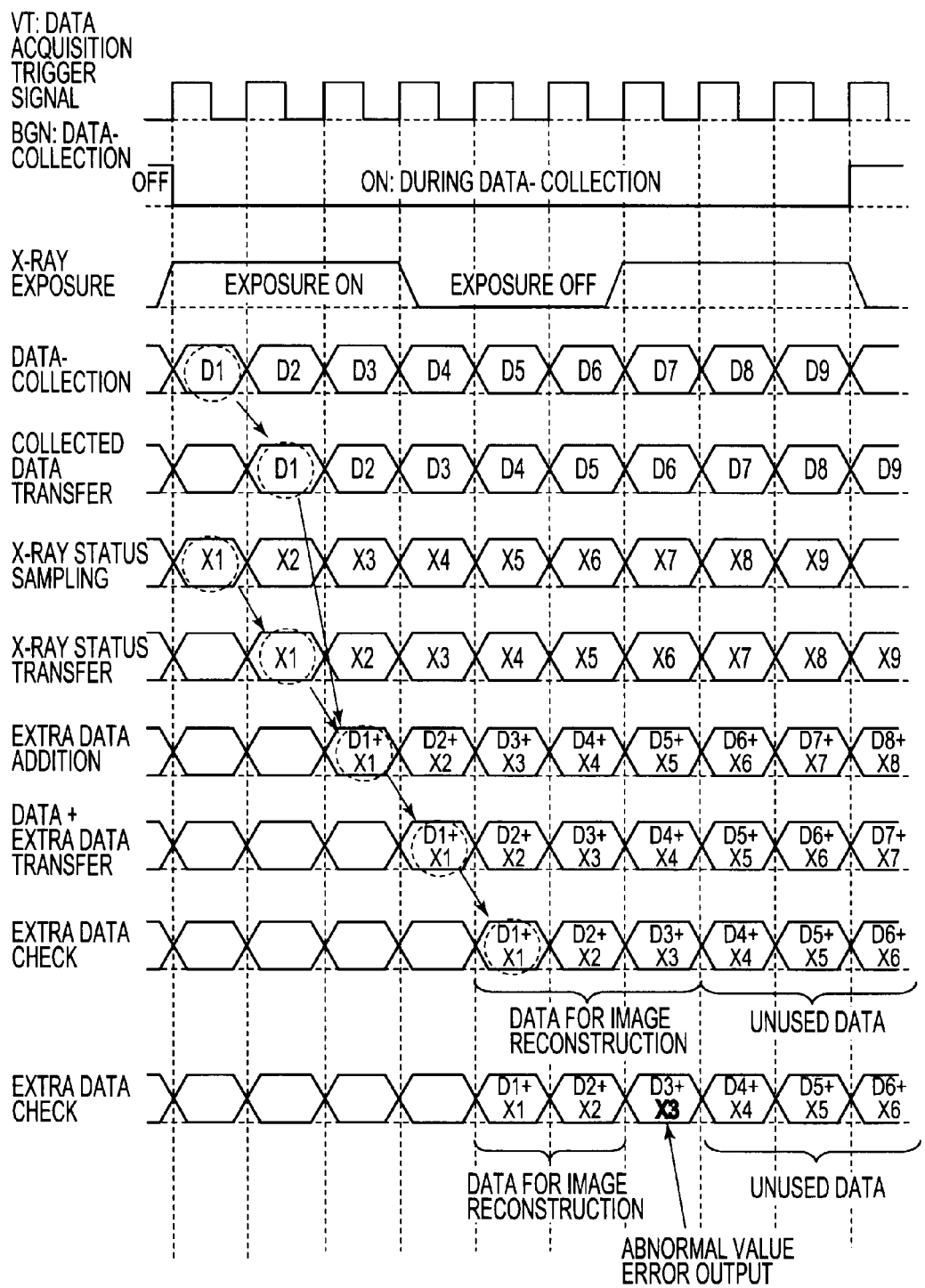
FIG. 2 is a timing chart of an action by an X-ray CT apparatus according to the embodiment of the present invention.

The gantry controller 10 generates a VT signal representing the collection timing for the projection data used by the data acquisition system 15 and outputs the VT signal to the data acquisition system 15 and the high-voltage generator 12 (FIG. 2; VT: data acquisition trigger signal). In addition, the gantry controller 10 generates a data-collection starting signal (BGN) representing the start of the collection of the projection data and outputs the data-collection starting signal (BGN) to the data acquisition system 15. Moreover, the gantry controller 10 outputs the control data to the high-voltage generator 12. The control data includes the information representing the conditions for X-ray exposures (tube current value and tube voltage value) and information representing the irradiation timing (ON/OFF signals of the X-ray exposure). In this embodiment, the projection data is collected by the data acquisition system 15 at a timing shorter than the ON period of the X-ray exposure. In other words, the projection data is continuously collected by the data acquisition system 15 at a collection timing shorter than the period during which X-rays are exposed to the X-ray tube 13 (ON period of the X-ray exposure).

Upon receiving the data-collection starting signal (BGN) from the gantry controller 10, the data acquisition system 15 starts the collection of the projection data and collects the projection data in synchronization with the VT signal (FIG. 2; ON: during the data collection).

The high-voltage generator 12 supplies, to the X-ray tube 13, the tube current and tube voltage represented by the exposure conditions according to the information represented by the irradiation timing (ON/OFF signals of the X-ray exposure) and causes the X-ray tube 13 to expose X-rays. The high-voltage generator 12 supplies the tube current and tube voltage to the X-ray tube 13 during periods in which the irradiation timing indicates that the X-ray exposure is in the ON state (FIG. 2; exposure ON) and causes the X-ray tube 13 to expose X-rays. In addition, the high-voltage generator 12 stops supplying the tube current and tube voltage to the X-ray tube 13 during periods in which the irradiation timing indicates that the X-ray exposure is in the OFF state (FIG. 2; exposure OFF).

The data acquisition system 15 collects, as the projection data, the X-rays detected by the X-ray detector 14 in synchronization with the VT signal output by the gantry controller 10 and outputs the projection data to the gantry controller 10. In FIG. 2, as one example, the data acquisition system 15 collects projection data D1, projection data D2, projection data D3, projection data D4 [ . . . ] and outputs these projection data to the gantry controller 10 (FIG. 2; data collection and collection data transfer). In the example shown in FIG. 2, the projection data D1, D2, D3, D7, D8, and D9 are data that have been collected at a timing during which the X-ray exposure is in the ON state. On the other hand, the projection data D4, D5, and D6 are data that have been collected at a timing during which the X-ray exposure is in the OFF state.

Meanwhile, the high-voltage generator 12 generates, in synchronization with the VT signal, the X-ray status information representing the tube current value (mA) and tube voltage value (kV) with which the X-ray tube 13 has actually exposed X-rays and outputs the X-ray status information to the gantry controller 10. In FIG. 2, as one example, the high-voltage generator 12 generates X-ray status information X1, X-ray status information X2, X-ray status information X3 [ . . . ] and outputs these items of X-ray status information to the gantry controller 10 (FIG. 2; X-ray status sampling, X-ray status transfer).

The data adding part 11 adds, as extra data, the X-ray status information generated by a VT signal identical to the VT signal representing the collection timing of the projection data for each view as well as the X-ray controlling data. In FIG. 2, as one example, the data adding part 11 adds, to the projection data D1, X-ray status information X1 generated from the VT signal identical to the VT signal representing the collection timing of the projection data D1. In addition, as the projection data D1 is data that has been collected at a timing during which the X-ray exposure is in the ON state, the data adding part 11 adds the ON signal of the X-ray exposure to the projection data D1. Similarly, the data adding part 11 adds, to the projection data D2, the X-ray status information X2 and the ON signal of the X-ray exposure. Moreover, the data adding part 11 adds, to the projection data D3, the X-ray status information X3 and the ON signal of the X-ray exposure.

In addition, the data adding part 11 adds the X-ray status information X4 to the projection data D4. As the projection data D4 is data that has been collected at a timing during which the X-ray exposure is in the OFF state, the data adding part 11 adds the OFF signal of the X-ray exposure to the projection data D4. Similarly, the data adding part 11 adds, to the projection data D5, the X-ray status information X5 and the OFF signal of the X-ray exposure and adds, to the projection data D6, the X-ray status information X6 and the OFF signal of the X-ray exposure. The gantry controller 10 thus outputs each projection data to which the extra data has been added to the preprocessing part 21 in the console part 2 (FIG. 2; extra data addition, data+extra data transfer).

The first verifying part 22 in the preprocessing part 21 receives, from the gantry controller 10, each projection data to which the extra data has been added. The first verifying part 22 verifies the X-ray status information (tube current value and tube voltage value) and the X-ray controlling data (ON/OFF signals of the X-ray exposure) that are included in the extra data. First, the first verifying part 22, based on the ON/OFF signals of the X-ray exposure represented by the X-ray controlling data, determines whether the projection data has been collected during X-ray exposure. In the example shown in FIG. 2, the projection data D1, D2, and D3 are added with the ON signals of the X-ray exposure and the first verifying part 22 determines that the projection data D1, D2, and D3 have been collected during X-ray exposure (FIG. 2; extra data check). On the other hand, the projection data D4, D5, and D6 are added with the OFF signals of the X-ray exposure and the first verifying part 22 determines that the projection data D4, D5, and D6 have been collected during discontinuation of X-ray exposure (FIG. 2; extra data check).

In addition, for projection data to which the ON signal of the X-ray exposure is added, the first verifying part 22 determines whether the tube current value and tube voltage value represented by the X-ray status information are within the specified range that has been preliminarily set. In the example shown in FIG. 2, the first verifying part 22 determines that for the projection data D1 and the projection data D2, the tube current value and tube voltage value are within the specified range. On the other hand, the first verifying part 22 determines that for the projection data D3, the tube current value and tube voltage value are not within the specified range (FIG. 2; extra data check).

Then, the preprocessing part 21 performs preprocessing, such as sensitivity correction and X-ray intensity correction, for the projection data in which the tube current value and tube voltage value are within the specified range. In the example shown in FIG. 2, the preprocessing part 21 performs preprocessing for the projection data D1 and D2. The preprocessing part 21 causes the projection-data memory part 23 to store the projection data for which the preprocessing has been performed. In the example shown in FIG. 2, the preprocessing part 21 causes the projection-data memory part 23 to store the projection data D1 and D2. The preprocessing part 21 may delete the projection data D3-6, for which the preprocessing has not been performed.

The reconstruction processing part 24 retrieves, from the projection-data memory part 23, the projection data for which the preprocessing has been performed and reconstructs the image data by performing a back-projection process for projection data. The display controller 27 causes the display part 29 to display the image based on the reconstructed image data.

Even for projection data to which the ON signal of the X-ray exposure is added, the preprocessing part 21 may output an error signal to the scan controller 20 if it is verified that the projection data is data in which the tube current value and tube voltage value are not within the specified range. In the example shown in FIG. 2, for the projection data D3, the tube current value and tube voltage value are not within the specified range. Therefore, upon verifying the projection data D3, the preprocessing part 21 outputs the error signal to the scan controller 20. The scan controller 20 issues an instruction to cancel the scan to the gantry controller 10 and outputs the error signal to the display controller 27. The scan is thus cancelled and the error information is displayed.

As described above, because the ON/OFF signal of the X-ray exposure is added to each projection data, the X-ray CT apparatus according to this embodiment allows projection data that may be used for reconstruction to be judged accurately. For example, when switching the X-ray exposure on and off and repetitively performing imaging as in a prospective gating scan synchronized with an electrocardiograph, it is possible to reconstruct an image using only projection data that has been collected with X-ray exposure in the ON state. In other words, when the data acquisition system 15 continuously performs the data collection while the X-ray tube 13 intermittently performs the X-ray exposure, projection data that may be used for reconstruction (projection data that has been collected with X-ray exposure in the ON state) can be judged more accurately. As a result, it is possible to reconstruct an image using only projection data that has been collected with X-ray exposure in the ON state.

In addition, in this embodiment, the tube current value and tube voltage value that have actually been supplied to the X-ray tube 13 are added to each projection data. This makes it possible to verify whether the high-voltage generator 12 and the X-ray tube 13 provide accurately outputs in response to instructions for intermittent X-ray exposure. In addition, even in cases in which the X-rays are exposed by the X-ray tube 13 while the X-ray output (mA) is modulated, the actual output value (mA) can be identified for each projection data for each view and the dose may thus be obtained accurately.

MODIFIED EXAMPLE 1

The X-ray CT apparatus and a method of controlling the X-ray CT apparatus according to Modified Example 1 will be described with reference to FIG. 3. In Modified Example 1, the tube voltage is supplied to the X-ray tube 13 by changing the tube voltage value at a specified switch timing. For example, X-rays are exposed by changing the tube voltage value for each one view. Alternatively, X-rays may be exposed by changing the tube voltage value each time the X-ray tube 13 and the X-ray detector 14 rotate once about the subject.

For example, the tube voltage is supplied to the X-ray tube 13 by switching, for each one view, the high voltage value (first voltage value) and low voltage value (second voltage value). When imaging is performed by changing the tube voltage values, differences in projection data (CT values) appear in some places. For example, locations where arteriosclerosis has occurred feature deposits of calcium (Ca). When imaging is performed by changing the tube voltage values, differences in the projection data (CT values) occur in the locations where calcium is deposited. Specifically, differences in the data of the locations where calcium is deposited are caused in projection data obtained by imaging with a high voltage value and projection data obtained by imaging with a low voltage value. The differences in the projection data make it possible to verify whether arteriosclerosis is present and to identify the locations where arteriosclerosis has occurred by comparing these data.

Switching of the tube voltage value is performed based on the control data output by the scan controller 20. For example, the scan controller 20 switches, for each one view, the tube voltage value included in the exposure conditions between a high voltage value and a low voltage value and outputs the control data to the gantry controller 10. The gantry controller 10 outputs the control data to the high-voltage generator 12. The high-voltage generator 12 supplies, according to the control data, the tube voltage to the X-ray tube 13 by switching, for each one view, the tube voltage value between the high voltage value and the low voltage value. The X-ray tube 13 thus exposes X-rays by switching, for each one view, the tube voltage value between the high voltage value and the low voltage value.

It is noted that an operator may arbitrarily change the tube voltage value using an operating part (not shown). Specifically, the operator inputs a high voltage value and a low voltage value using the operating part and the high voltage value and the low voltage value are thereby output to the scan controller 20. In addition, the operator may use the operating part to change the switch timing for switching the tube voltage value. The operator may use the operating part to set a switch timing for each one view or for one rotation. The operator uses the operating part to input the switch timing and the information representing the switch timing is thereby output to the scan controller 20.

The high-voltage generator 12 includes, as the tube voltage value, the high voltage value or the low voltage value in the X-ray status information and outputs the X-ray status information to the gantry controller 10. The data adding part 11 adds, as the extra data, the X-ray status information and the X-ray controlling data to the projection data for each view.

Figure 3:
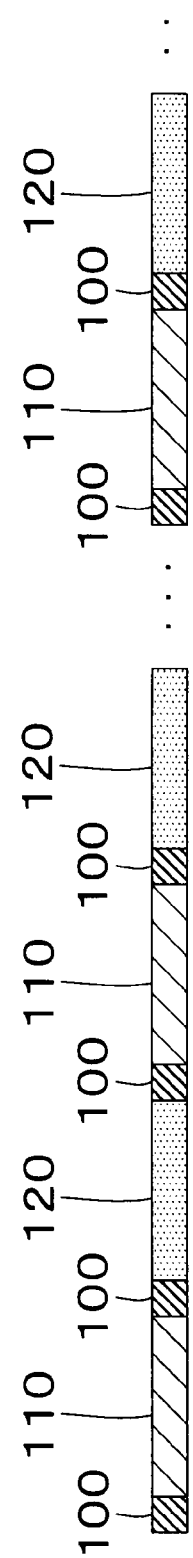
FIG. 3 shows a structure of projection data obtained from a different tube voltages.

FIG. 3 shows one example of the projection data obtained by switching the tube voltage value for each one view. The projection data 110 is data obtained with a high voltage value and the projection data 120 is data obtained with a low voltage value. The extra data 100 is added to each projection data as the additional information.

According to the tube voltage value included in the status information, the first verifying part 22 differentiates between the projection data obtained with the high voltage value and the projection data obtained with the low voltage value. In the example shown in FIG. 3, the first verifying part 22 refers to each of the extra data 100 added to the projection data 110 and the projection data 120 and differentiates between the projection data 110 obtained with the high voltage value and the projection data 120 obtained with the low voltage value. It is noted that the second verifying part 25 may perform this process.

Projection data 110 and projection data 120 may be used to confirm existence of arteriosclerosis and to identify the occurring area of arteriosclerosis. In other words, when arteriosclerosis occurs, data is different in the area of arteriosclerosis occurrence, between the case of projection data 110 obtained from high voltage value and the case of projection data 120 obtained from low voltage value. The difference of these data allows confirmation of existence of arteriosclerosis and identification of places of arteriosclerosis occurrence.

For example, a processor (not shown) may automatically identify positions where differences in projection data occur. In other words, the processor may compare the projection data 110 with projection data 120 to identify the position of different data as the place where arteriosclerosis occurs.

The display controller 27 may cause the display 29 to display information of whether arteriosclerosis exists or not. Further, the display controller 27 may identify portions of arteriosclerosis occurrence in the image, which is displayed by the display 29 through the control of the display controller 27.

The reconstruction processing part 24 may reconstruct first image data using the projection data obtained with the high voltage value. In addition, the reconstruction processing part 24 may reconstruct second image data using the projection data obtained with the low voltage value. In the example shown in FIG. 3, the reconstruction processing part 24 reconstructs the first image data using the projection data 110 and reconstructs the second image data using the projection data 120.

The first image and the second image may be used to verify whether arteriosclerosis is present or to identify the locations where arteriosclerosis has occurred. That is, when arteriosclerosis has occurred, the CT values of the locations where arteriosclerosis has occurred differ between the first image obtained with the high voltage value and the second image obtained with the low voltage value. The differences in the CT values make it possible to verify whether arteriosclerosis is present or to identify the locations where arteriosclerosis has occurred. For example, differences in the CT values are displayed as differences in darkness in the images, and therefore, based on such differences in darkness, it is possible to verify whether arteriosclerosis is present.

A processor (not shown) may automatically identify positions where differences in image data occur. In other words, the processor may compare the first image data with the second image data to identify the position of different CT values as the place where arteriosclerosis occurs.

The display controller 27 may cause the display 29 to display the first image based on the first image data and the second image based on the second image data in parallel. Further, the display controller 27 may identify portions of arteriosclerosis occurrence in the image, which is displayed by the display 29 through the control of the display controller 27.

As described above, by adding the tube voltage value as the additional information to each projection data, even when imaging is performed by changing the tube voltage values at the specified switch timing, each projection data may be distinguished for extraction.

Further, for reconstruction processing, each projection data may be distinguished for extraction so that the image data are reconstructed.

In other words, even when imaging is performed using different tube voltage values, projection data obtained with the same tube voltage value may be identified.

MODIFIED EXAMPLE 2

The X-ray CT apparatus and a method of controlling the X-ray CT apparatus according to Modified Example 2 will be described with reference to FIG. 4. In Modified Example 2, the X-ray exposure is controlled based on cardiac signals (electrocardiogram (ECG) signals).

In the case of using ECG signals, the ECG signals of the subject are obtained by an electrocardiograph 4 as shown in FIG. 1. It is noted that the electrocardiograph 4 may not be provided in cases in which the X-ray exposure is not performed using ECG signals.

The electrocardiograph 4 obtains an ECG signal of the subject and outputs the ECG signal to the scan controller 20. The scan controller 20 controls the high-voltage generator 12 so that X-rays are exposed for a period that has been preliminary set (imaging period) based on the ECG signal. The period for which X-rays are exposed (imaging period) may be preliminarily set and set in the scan controller 20 or arbitrarily set by the operator. For example, when the operator specifies, using an operating part (not shown), the period for which X-rays are exposed, information representing the specified period is output from the operating part to the scan controller 20. For example, when cardiac diastole and systole are specified as an imaging period, the scan controller 20 identifies the diastole and systole based on the ECG signal and controls the high-voltage generator 12 so that X-rays are exposed for the imaging period.

As described above, the high-voltage generator 12 includes the tube current value in the X-ray status information and outputs the X-ray status information to the gantry controller 10. The data adding part 11 adds, as the extra data, the X-ray status information and X-ray controlling data to the projection data for each view.

Figure 4:
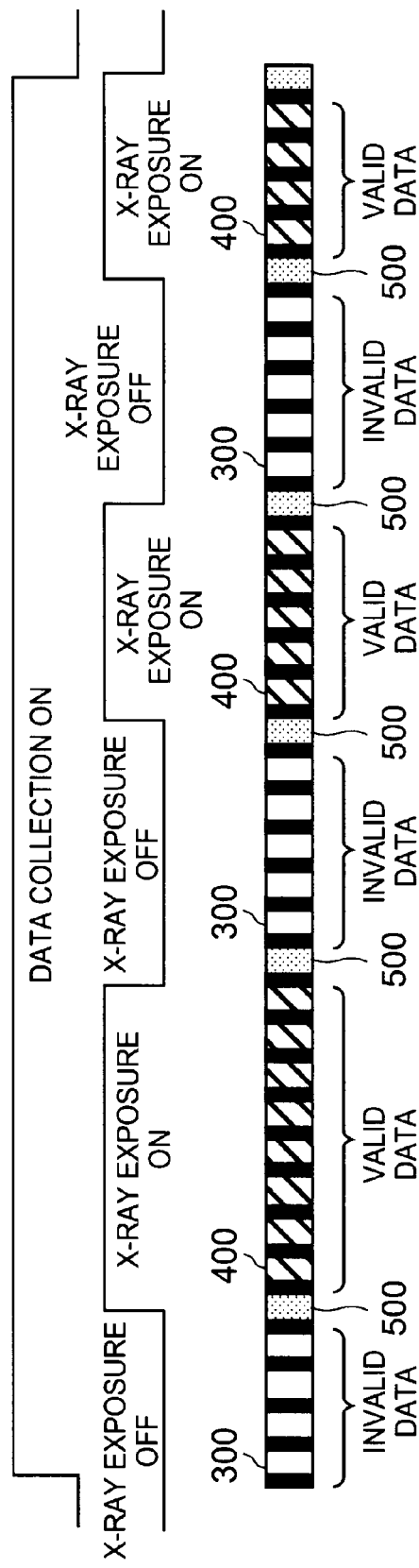
FIG. 4 shows a structure of projection data obtained through imaging synchronized with electrocardiographic signal.

FIG. 4 shows one example of a timing for X-ray exposure and the projection data. The projection data 300 is data that has been collected during a period in which X-rays are not exposed. In FIG. 4, the projection data 300 is shown as invalid data. The projection data 400 is data that has been collected during a period in which X-rays have been exposed. In FIG. 4, the projection data 400 is shown as valid data. The projection data 500 is data collected at timing at which the X-ray exposure is switched between on and off. The extra data is added to each of the projection data 300, 400, and 500 as the additional information.

Based on the tube current value included in the status information, the first verifying part 22 specifies, as valid data, project data collected during periods in which X-rays have been exposed. For example, the first verifying part 22 identifies, as the valid data, projection data in which the tube current value is within the specified range that has been preliminary set. This specified range is a criterion for determining whether the tube current value is a normal value during X-ray exposure. When the tube current value is within the specified range, the first verifying part 22 determines that the X-ray exposure has been performed with a normal tube current value. In other words, the first verifying part 22 determines that projection data in which the values are within the specified range is projection value that has been collected during normal X-ray exposure. In the example shown in FIG. 4, the first verifying part 22 identifies, with reference to each of the extra data added to the projection data 300, 400, and 500, the projection data 400 in which the tube current value is within the specified range as the valid data. It is noted that the second verifying part 25 may perform this process.

The reconstruction processing part 24 reconstructs the image data using the projection data that has been identified as the valid data.

In the example shown in FIG. 4, the reconstruction processing part 24 reconstructs the image data using the projection data 400. The display controller 27 causes the display part 29 to display the image based on the image data.

In cases of switching the X-ray exposure on and off based on cardiac signals, projection data collected at a switch timing for switching the X-ray exposure on and off is data that has been collected under conditions in which the X-rays are unstable. In other words, X-rays exposed from the X-ray tube 13 become unstable at the timing at which the X-rays rise (from the OFF state to the ON state) and the timing at which the X-rays decline (from ON state to OFF state).

Therefore, projection data collected at the switch timing for switching the X-ray exposure on and off becomes data collected under conditions in which the X-rays are unstable. In the example shown in FIG. 4, as the projection data 500 is collected at the switch timing for switching the X-ray exposure on and off, it is data that has been collected under conditions in which the X-rays are unstable.

According to this Modified Example 2, the tube current value is added to each project data as the additional information, thus making it possible to identify valid projection data while avoiding projection data collected at a timing at which the X-rays are unstable. The image data may thus be reconstructed using valid projection data.

In the prior art, by setting a threshold relative to the detection value of a Ref detector, projection data collected during periods in which X-rays have been exposed is identified. However, in methods using an Ref detector, there is a possibility that projection data collected at a switch timing for switching the X-ray exposure on and off may be extracted and used for reconstruction.

In contrast, in the X-ray CT apparatus according to this Modified Example 2, the tube current value is added to the project data as the additional information, thus making it possible to identify valid projection data based on the tube current value and reconstruct the image data.

What is claimed is:

1. An X-ray CT apparatus comprising:
an X-ray generator;
an X-ray detector, arranged opposite to said X-ray generator by sandwiching a subject, configured to collect, as projection data, X-rays that have been exposed from said X-ray generator and transmitted through said subject at a specified collection timing, wherein
said X-ray generator and said X-ray detector are configured to be rotatable about said subject;
a controller configured to control the timing of exposing said X-rays from said X-ray generator so as to supply a voltage and current to said X-ray generator to cause said X-ray generator to expose said X-rays when said X-ray generator exposes said X-rays, to control the collection timing to cause said X-ray detector to continuously collect said projection data at said specified collection timing, and to cause additional information representing the state of exposure of said X-rays to be added to each projection data that has been collected by said X-ray detector at said specified collection timing;
an identifying part configured to identify the projection data to be used for generating image data, based on said additional information, upon receiving said each projection data to which said additional information has been added; and
an image generator configured to generate the image data using said projection data that has been identified by said identifying part;
wherein:
said controller is further configured to cause exposure information representing whether said X-rays have been exposed by said X-ray generator to be added to each projection data as said additional information; and
said identifying part is further configured to identify the projection data collected by said X-ray detector at the timing at which said X-rays have been exposed, based on said exposure information, upon receiving said each projection data to which said exposure information has been added.

2. An X-ray CT apparatus comprising:
an X-ray generator;
an X-ray detector, arranged opposite to said X-ray generator by sandwiching a subject, configured to collect, as projection data, X-rays that have been exposed from said X-ray generator and transmitted through said subject at a specified collection timing, wherein
said X-ray generator and said X-ray detector are configured to be rotatable about said subject;
an identifying part configured to identify the projection data to be used for generating image data, based on said additional information, upon receiving said each projection data to which said additional information has been added;
an image generator configured to generate the image data using said projection data that has been identified by said identifying part; and
a controller configured to control the timing of exposing said X-rays from said X-ray generator so as to supply a voltage and current to said X-ray generator to cause said X-ray generator to expose said X-rays when said X-ray generator exposes said X-rays, to control the collection timing to cause said X-ray detector to continuously collect said projection data at said specified collection timing, and to cause additional information representing the state of exposure of said X-rays to be added to each projection data that has been collected by said X-ray detector at said specified collection timing;
wherein:
said controller is further configured to cause the values of said voltage and said current supplied to said X-ray generator to be added to said each projection data as said additional information; and
said identifying part is further configured to identify said projection data to be used for generating said image data, based on the values of said voltage and said current, upon receiving said each projection data to which the values of said voltage and said current have been added.

3. An X-ray CT apparatus comprising:
an X-ray generator;
an X-ray detector, arranged opposite to said X-ray generator by sandwiching a subject, configured to collect, as projection data, X-rays that have been exposed from said X-ray generator and transmitted through said subject at a specified collection timing, wherein
said X-ray generator and said X-ray detector are configured to be rotatable about said subject;
a controller configured to control the timing of exposing said X-rays from said X-ray generator so as to supply a voltage and current to said X-ray generator to cause said X-ray generator to expose said X-rays when said X-ray generator exposes said X-rays, to control the collection timing to cause said X-ray detector to continuously collect said projection data at said specified collection timing, and to cause additional information representing the state of exposure of said X-rays to be added to each projection data that has been collected by said X-ray detector at said specified collection timing;
an identifying part configured to identify the projection data to be used for generating image data, based on said additional information, upon receiving said each projection data to which said additional information has been added; and
an image generator configured to generate the image data using said projection data that has been identified by said identifying part;
wherein:
said controller is further configured to cause the exposure information representing whether said X-rays have been exposed by said X-ray generator as well as the values of said voltage and said current supplied to said X-ray generator to be added to said each projection data as said additional information; and
said identifying part is further configured to identify, based on said exposure information, the projection data collected by said X-ray detector at the timing at which said X-rays have been exposed and then identifies, from among said projection data collected by said X-ray detector at the timing at which said X-rays were exposed, projection data in which the values of said voltage and said current are within the specified range that has been preliminarily set upon receiving said each projection data to which said additional information has been added.

4. The X-ray CT apparatus according to claim 3, wherein said controller is configured to stop supplying said voltage and said current to said X-ray generator and to cause said X-ray detector to stop collecting said projection data when projection data in which the values of said voltage and said current are not within said specified range is identified.

5. The X-ray CT apparatus according to claim 4, further comprising:
an informing part configured to inform that said projection data in which the values of said voltage and said current are not within said specified range voltage has been identified.

6. An X-ray CT apparatus comprising:
an X-ray generator;
an X-ray detector, arranged opposite to said X-ray generator by sandwiching a subject, configured to collect, as projection data, X-rays that have been exposed from said X-ray generator and transmitted through said subject at a specified collection timing, wherein
said X-ray generator and said X-ray detector are configured to be rotatable about said subject;
a controller configured to control the timing of exposing said X-rays from said X-ray generator so as to supply a voltage and current to said X-ray generator to cause said X-ray generator to expose said X-rays when said X-ray generator exposes said X-rays, to control the collection timing to cause said X-ray detector to continuously collect said projection data at said specified collection timing, and to cause additional information representing the state of exposure of said X-rays to be added to each projection data that has been collected by said X-ray detector at said specified collection timing;
an identifying part configured to identify the projection data to be used for generating image data, based on said additional information, upon receiving said each projection data to which said additional information has been added;
an image generator configured to generate the image data using said projection data that has been identified by said identifying part; and
an identifying part, wherein:
said controller is further configured to cause the exposure information representing whether said X-rays have been exposed by said X-ray generator as well as the values of said voltage and said current supplied to said X-ray generator to be added to said each projection data as said additional information;
said identifying part is further configured to identify, based on said exposure information and upon receiving said each projection data to which said additional information has been added, the projection data collected by said X-ray detector at the timing at which said X-rays have been exposed and then identifies, from among said projection data collected by said X-ray detector at the timing at which said X-rays were exposed, whether there is projection data in which the values of said voltage and said current are not within the specified range that has been preliminarily set; and
said controller is further configured to stop supplying said voltage and said current to said X-ray generator and to cause said X-ray detector to stop collecting said projection data when projection data in which the values of said voltage and said current are not within said specified range is identified.

7. A method of controlling an X-ray CT apparatus, the X-ray CT apparatus comprising:
an X-ray generator;
an X-ray detector, arranged opposite to said X-ray generator by sandwiching a subject, configured to collect, as projection data, X-rays that have been exposed from said X-ray generator and transmitted through said subject at a specified collection timing, wherein
said X-ray generator and said X-ray detector are configured to be rotatable about said subject, and the method comprising:
controlling the timing of exposing said X-rays from said X-ray generator so as to supply a voltage and current to said X-ray generator to cause said X-ray generator to expose said X-rays when said X-ray generator exposes said X-rays;
controlling the collection timing to cause said X-ray detector to continuously collect said projection data at said specified collection timing;
causing additional information representing the state of exposure of said X-rays to be added to each projection data that has been collected by said X-ray detector at said specified collection timing;
identifying the projection data to be used for generating image data, based on said additional information, upon receiving said each projection data to which said additional information has been added; and
generating the image data using said identified projection data;
wherein:
exposure information representing whether said X-rays have been exposed by said X-ray generator is caused to be added to each projection data as said additional information; and
the projection data collected by said X-ray detector at the timing at which said X-rays have been exposed, is identified based on said exposure information, upon receiving said each projection data to which said exposure information has been added.

8. A method of controlling an X-ray CT apparatus, the X-ray CT apparatus comprising:
an X-ray generator;
an X-ray detector, arranged opposite to said X-ray generator by sandwiching a subject, configured to collect, as projection data, X-rays that have been exposed from said X-ray generator and transmitted through said subject at a specified collection timing, wherein
said X-ray generator and said X-ray detector are configured to be rotatable about said subject, and the method comprising:
controlling the timing of exposing said X-rays from said X-ray generator so as to supply a voltage and current to said X-ray generator to cause said X-ray generator to expose said X-rays when said X-ray generator exposes said X-rays;
controlling the collection timing to cause said X-ray detector to continuously collect said projection data at said specified collection timing;
causing additional information representing the state of exposure of said X-rays to be added to each projection data that has been collected by said X-ray detector at said specified collection timing;

identifying the projection data to be used for generating image data, based on said additional information, upon receiving said each projection data to which said additional information has been added; and generating the image data using said identified projection data;

wherein:

the values of said voltage and said current supplied to said X-ray generator are caused to be added to said each projection data as said additional information; and said projection data to be used for generating said image data, is identified based on the values of said voltage and said current, upon receiving said each projection data to which the values of said voltage and said current have been added.

9. A method of controlling an X-ray CT, the X-ray CT apparatus comprising:

an X-ray generator;

an X-ray detector, arranged opposite to said X-ray generator by sandwiching a subject, configured to collect, as projection data, X-rays that have been exposed from said X-ray generator and transmitted through said subject at a specified collection timing, wherein said X-ray generator and said X-ray detector are configured to be rotatable about said subject, and the method comprising:

controlling the timing of exposing said X-rays from said X-ray generator so as to supply a voltage and current to said X-ray generator to cause said X-ray generator to expose said X-rays when said X-ray generator exposes said X-rays;

controlling the collection timing to cause said X-ray detector to continuously collect said projection data at said specified collection timing;

causing additional information representing the state of exposure of said X-rays to be added to each projection data that has been collected by said X-ray detector at said specified collection timing;

identifying the projection data to be used for generating image data, based on said additional information, upon receiving said each projection data to which said additional information has been added; and generating the image data using said identified projection data;

wherein:

the exposure information representing whether said X-rays have been exposed by said X-ray generator as well as the values of said voltage and said current supplied to said X-ray generator is caused to be added to said each projection data as said additional information; and projection data is identified from among said projection data collected by said X-ray detector at the timing at which said X-rays were exposed, so that the projection data is identified in which the values of said voltage and said current are within the specified range that has been preliminarily set, based on said exposure information, upon receiving said each projection data to which said additional information has been added.

10. The method of controlling the X-ray CT apparatus according to claim 9, wherein supplying said voltage and said current to said X-ray generator is stopped and said X-ray detector is caused to stop collecting said projection data when projection data in which the values of said voltage and said current are not within said specified range is identified.

11. The method of controlling the X-ray CT apparatus according to claim 10, further comprising:

informing that said projection data in which the values of said voltage and said current are not within said specified range voltage has been identified.

12. A method of controlling an X-ray CT apparatus, the X-ray CT apparatus comprising:

an X-ray generator;

an X-ray detector, arranged opposite to said X-ray generator by sandwiching a subject, configured to collect, as projection data, X-rays that have been exposed from said X-ray generator and transmitted through said subject at a specified collection timing, wherein said X-ray generator and said X-ray detector are configured to be rotatable about said subject, and the method comprising:

controlling the timing of exposing said X-rays from said X-ray generator so as to supply a voltage and current to said X-ray generator to cause said X-ray generator to expose said X-rays when said X-ray generator exposes said X-rays;

controlling the collection timing to cause said X-ray detector to continuously collect said projection data at said specified collection timing; and causing additional information representing the state of exposure of said X-rays to be added to each projection data that has been collected by said X-ray detector at said specified collection timing;

wherein:

the exposure information representing whether said X-rays have been exposed by said X-ray generator as well as the values of said voltage and said current supplied to said X-ray generator is caused to be added to said each projection data as said additional information, the method further comprising:

identifying, based on said exposure information and upon receiving said each projection data to which said additional information has been added, the projection data collected by said X-ray detector at the timing at which said X-rays have been exposed and then identifies, from among said projection data collected by said X-ray detector at the timing at which said X-rays were exposed, whether there is projection data in which the values of said voltage and said current are not within the specified range that has been preliminarily set; wherein supplying said voltage and said current to said X-ray generator is stopped and said X-ray detector is caused to stop collecting said projection data when projection data in which the values of said voltage and said current are not within said specified range is identified.

* * * * *